United States Patent
Klussmann et al.

(10) Patent No.: US 9,399,621 B2
(45) Date of Patent: Jul. 26, 2016

(54) PROCESS FOR PREPARING SUBSTITUTED INDOLE DERIVATIVES

(71) Applicant: STUDIENGESELLSCHAFT KOHLE MBH, Mülheim an der Ruhr (DE)

(72) Inventors: Martin Klussmann, Duesseldorf (DE); Naeem Gulzar, Mülheim an der Ruhr (DE)

(73) Assignee: STUDIENGESELLSCHAFT KOHLE MBH, Mülheim an der Ruhr (DE)

( * ) Notice: Subject to any disclaimer, the term of this patent is extended or adjusted under 35 U.S.C. 154(b) by 0 days.

(21) Appl. No.: 14/416,656

(22) PCT Filed: Jul. 23, 2013

(86) PCT No.: PCT/EP2013/065511
§ 371 (c)(1),
(2) Date: Jan. 23, 2015

(87) PCT Pub. No.: WO2014/016296
PCT Pub. Date: Jan. 30, 2014

(65) Prior Publication Data
US 2015/0203451 A1    Jul. 23, 2015

(30) Foreign Application Priority Data
Jul. 25, 2012 (EP) .................................... 12177762

(51) Int. Cl.
| | | |
|---|---|---|
| *C07D 209/88* | (2006.01) | |
| *C07D 401/04* | (2006.01) | |
| *C07D 417/04* | (2006.01) | |
| *C07D 209/14* | (2006.01) | |
| *C07D 209/86* | (2006.01) | |
| *C07D 209/94* | (2006.01) | |
| *C07D 403/04* | (2006.01) | |

(52) U.S. Cl.
CPC ............ *C07D 209/88* (2013.01); *C07D 209/14* (2013.01); *C07D 209/86* (2013.01); *C07D 209/94* (2013.01); *C07D 401/04* (2013.01); *C07D 403/04* (2013.01); *C07D 417/04* (2013.01)

(58) Field of Classification Search
CPC .. C07D 209/14; C07D 209/86; C07D 209/08; C07D 209/948; C07D 209/88; C07D 401/04
See application file for complete search history.

(56) References Cited

FOREIGN PATENT DOCUMENTS

| WO | 03 101981 A1 | 12/2003 |
|---|---|---|
| WO | 2004 110999 A1 | 12/2004 |
| WO | 2006 065480 A2 | 6/2006 |
| WO | 2006 121467 A2 | 11/2006 |

OTHER PUBLICATIONS

Plant, J Chem Soc, Jan. 1933, pp. 955-960.*
Ihara, Tetrahedron, vol. 41, No. 11, 2109-2114, Jan. 1985.*
Grinev et al; "Synthesis and Biological Activity of 2-Aminoalkyl(Aryl)-3-Phenyl-5-Nitroindoles"; Pharmaceutical Chem Journal, Vo. 17, No. 9, pp. 635-642 (Jan. 1983).
Wilson et al.; "Nucleophilic Additions to Triazolinedione Ylides, Extremely Reactive Carbonyl Equivalents: A New Class of Condensation Reactions"; J. Org. Chem., vol. 52, No. 13, pp. 2699-2707 (Jun. 1987).
Plant, et ano.; "Addition Reactions of the Indole Nucleus"; Journal of the Chemical Society, pp. 955-960 (Jan. 1933).
Itahara et al.; The Oxidation of the 2-Methyl Group of 3-Substituted 2-Methylindoles by Autoxidation and with Silver Acetate in Carboxylic Acide; Bulletin of the Chem. Soc. Japan, vol. 55, pp. 3861-3864 (Jan. 1982).
Ihara et al.; "Conversion of Indoles into Quinolines Through the N-1-C2 Fission by Singlet-Oxygen as a Model Experiment of Biomimetic Synthesis of Quinine Alkaloids"; Tetrahedron vol. 41, No. 11, pp. 2109-2114 (Jan. 1985).
Nakagawa et al.: "A New Dynthesis of Beta-Carboline"; Tetrahedron Letters, vol. 24, No. 21, pp. 2171-2174 (Jan. 1983).
Vice et al.; "C-2 Side Chain Alkylation of 2-Methyl-3-Alkylindoles via 3-Methoxyindolenines" Tetrahedron Letters, vol. 22, No. 8, pp. 829-832 (Jan. 1982).

* cited by examiner

*Primary Examiner* — D M Seaman
(74) *Attorney, Agent, or Firm* — Norris McLaughlin & Marcus, P.A.

(57) ABSTRACT

The present invention relates to a process for preparing substituted indole derivatives. More particularly, the invention refers to a new method to synthesize indole-derivatives by oxidative C—H-functionalization.

8 Claims, No Drawings

PROCESS FOR PREPARING SUBSTITUTED INDOLE DERIVATIVES

This application is a 371 of PCT/EP2013/065511, filed Jul. 23, 2013, which claims foreign priority benefit under 35 U.S.C. §119 of the European Patent Application No. 12177762.7, filed Jul. 25, 2012, the disclosures of which are incorporated herein by reference.

The present invention relates to a process for preparing substituted indole derivatives. More particularly, the invention refers to a new method to synthesize indole-derivatives by oxidative C—H-functionalization.

Indole-derivatives such as tetrahydrocarbazoles are of particular interest for use as pharmaceuticals, in particular for treating viral infections.

For example, WO 2004-110999 A1 relates to tetrahydrocarbazoles derivatives that are useful in the treatment of human papillomaviruses, and also to the methods for the making and use of such compounds.

WO2006-121467A2 relates to compounds that are useful in the treatment of viruses belonging to Flaviviridae, including flaviviruses, pestiviruses, and hepaciviruses. The application includes compounds useful for the treatment or prophylaxis of dengue fever, yellow fever, West Nile virus, and HCV Besides an antiviral potential, said indole-derivatives may also be used in other pharmaceutical applications. WO2006-065480A2 relates to methods, compounds, and compositions for inhibiting angiogenesis. More particularly, the application relates to methods, compounds and compositions for inhibiting VEGF production.

Said indole compounds are obtainable on various synthetical routes. However, it is common to all routes that they are either complicated and comprise to many reaction steps or they lead to the final products in a yield which still to be optimized. It is therefore the task to provide a method that yields such indole compounds more easily and with a higher yield.

Surprisingly, the inventors found out that indole-derivatives with a C—H-residue in the 2-position can be coupled with various nucleophiles by using at least one catalyst, oxygen or air and solvents at room temperature, with or without irradiation by visible light. The used nucleophiles are particularly N—H-nucleophiles but can be O—H and C—H nucleophiles as well. Many of the products thus obtained are known pharmaceutical agents, especially antiviral agents (see previous patents). In a simple way, the inventive method can be represented as follows:

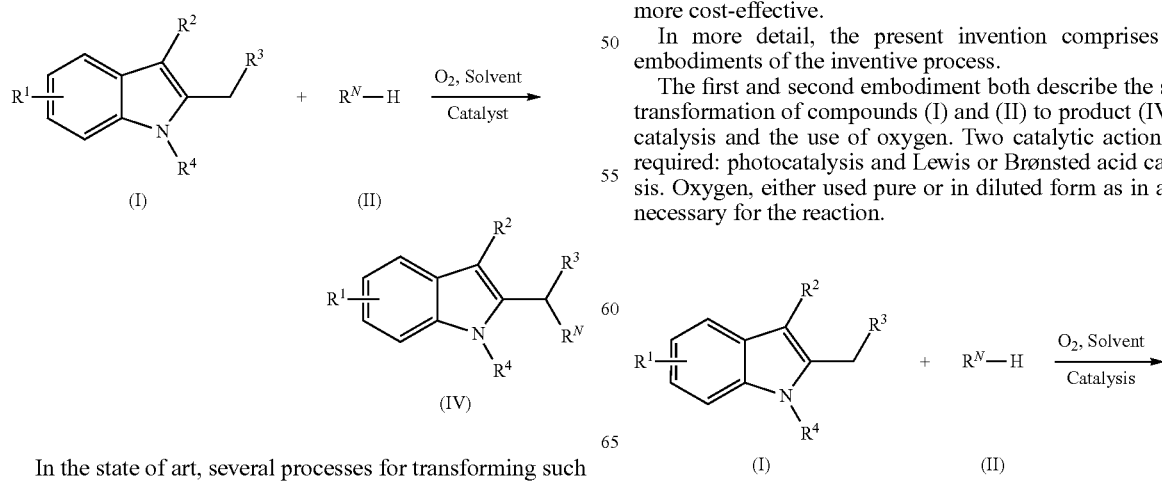

In the state of art, several processes for transforming such indole derivatives are known.

For example, Pharmaceutical. Chem. J., 17(9), 1983, 635-642 describes the transformation of indole derivatives like (I) into products like (IV), including compounds where $R^N$ equals a substituted nitrogen atom. In contrast to the present invention, no oxygen and no light is needed, but stoichiometric amounts of bromine are required.

WO03101981A1 describes, in Examples 58 and 59, transformations of an indole derivative like (I), the product from Example 27, into products like (IV) where $R^N$ equals substituted nitrogen atoms. In contrast to the invention, no oxygen and no light is needed, but stoichiometric amounts of N-bromosuccinimide are required as a brominating reagent.

Furthermore, J. Org. Chem., 52(13), 1987, 2699-2707 describes a transformation of an indole derivative like (I) into a product such as (IV), In contrast to the invention, no oxygen is needed., but stoichiometric amounts of a triazole compound, PTAD, which has to be synthesized by oxidation of 4-phenylurazole with tert-butyl hypochlorite, or stoichiometric amounts of tert-butyl hypochlorite and a base like triethylamine or DBU are needed.

J. Chem. Soc., 1933, 955 describes various transformations of indole derivatives. A single example in the paragraph bridging pages 958 and 959 is related to the invention. An indole like (I) is transformed into a product like (IV), where $R^N$ equals OH (hydroxy). In contrast to the invention, no oxygen and no light is needed, but stoichiometric amounts of bromine and silver oxide are required.

Chem. Soc. Japan, 55(12), 1982, 3861 describes a method that transforms an indole derivative like (I) into a product like (IV) by reaction with acetic acid in place of the nucleophilic reagent (II) wherein a stoichiometric amount of silver acetate is required for the reaction.

Tetrahedron, 41(11), 1985, 2109-2114 and Tetrahedron Letters, 24(21), 1983, 2171-2174 both refer to the oxidation of an indole derivative by action of a photocatalyst, oxygen and light, followed by a reduction to an alcohol by using dimethyl sulfide as a reductant, followed by acid catalysis to give the final de-hydroxylated product, The advantages of the inventive process on in comparison with the documents of the state of art can be easily seen. Whereas said documents of the state of art require at least one synthetic stoichiometric reagent such as bromine or brominating agents, a reactive organic triazolinedione or silver salts or dimethyl sulfide, the inventive process requires oxygen as the only stoichiometric reagent and additionally one or two catalysts and solvent. The invention requires less material, less process steps and the only stoichiometric reagent needed is oxygen, which has a low molecular weight and can be used in the form of air. The inventive process is therefore much more cost-effective.

In more detail, the present invention comprises two embodiments of the inventive process.

The first and second embodiment both describe the same transformation of compounds (I) and (II) to product (IV) by catalysis and the use of oxygen. Two catalytic actions are required: photocatalysis and Lewis or Brønsted acid catalysis. Oxygen, either used pure or in diluted form as in air, is necessary for the reaction.

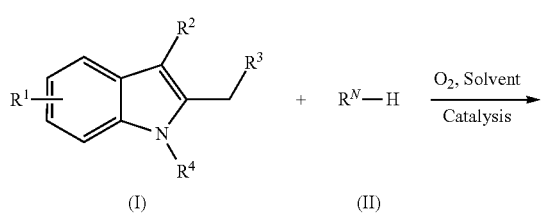

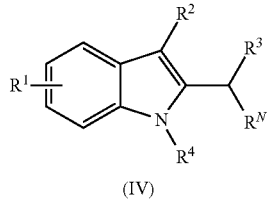

(IV)

In the first embodiment, this transformation is achieved as shown above in a single step. The preferred catalyst, iron phthalocyanine (FePc), combines the properties of a photocatalyst and a Lewis acid. Therefore, only one catalyst is required in this case.

In the second embodiment, this transformation is achieved in two separate steps. The first step is the oxidation of (I) by photocatalysis under oxygen to give intermediate (III). In the second step, acid catalysis converts (III) and (II) to the product (IV). The use of two catalysts is preferred for the second embodiment, for example using Rose Bengal as photocatalyst for the first step and a Brønsted acid like trifluoroacetic acid for the second step.

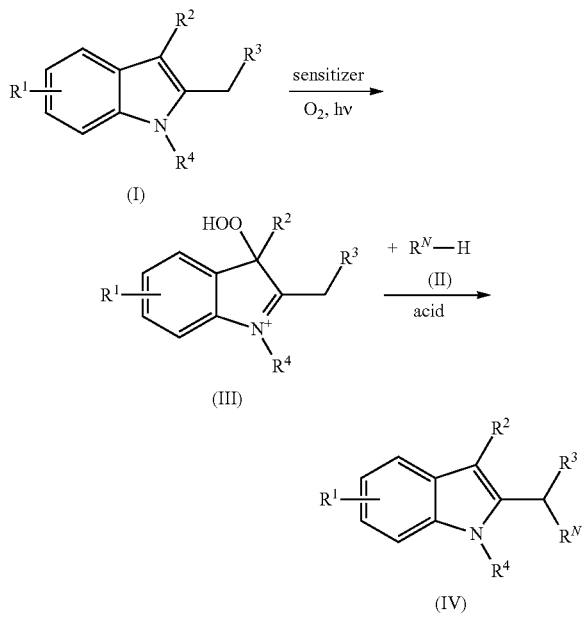

The intermediate (III) is believed to be formed under the conditions of the first embodiment, too.

In the formulae (I) to (IV), the substituents $R^1$ to $R^4$ and $R^N$ can have the following meanings. In that respect, the indication of $R^1$ is intended, throughout the specification and claims, to represent four substituents $R^{1a}$, $R^{1b}$, $R^{1c}$ and $R^{1d}$ which can be in any position of the aromatic ring as exemplified for compound (IV).

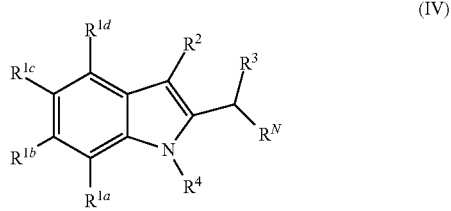

As indicated, $R^1$ represents four substituents $R^{1a}$, $R^{1b}$, $R^{1c}$ and $R^{1d}$ on the aromatic ring which substituents may be the same of different and may be selected each from hydrogen, heterosubstituents, $C_1$ to $C_{20}$ straight chain, branched chain or cyclic aliphatic hydrocarbons, optionally including hetero atoms and/or optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon or partially arene-hydrogenated forms such as aryl, aryl-($C_1$-$C_6$)-alkyl, heteroaryl-($C_1$-$C_6$)-alkyl, each heterosubstituent or hydrocarbon optionally being substituted by one or more groups selected from $C_1$ to $C_{20}$ straight chain, branched chain or cyclic aliphatic hydrocarbons, optionally including hetero atoms and/or optionally having one or more unsaturated bonds such as $C_1$-$C_{20}$-alkyl, $C_2$-$C_{20}$-alkenyl or $C_2$-$C_{20}$-alkinyl, or $C_6$ to $C_{20}$ aromatic hydrocarbon or partially arene-hydrogenated forms such as aryl, aryl-($C_1$-$C_6$)-alkyl, heteroaryl-($C_1$-$C_6$)-alkyl or heterosubstituents, or at least two of said $R^{1a}$, $R^{1b}$, $R^{1c}$ and $R^{1d}$ substituents may also form an aliphatic or heteroaliphatic ring structure having 4 to 10 ring atoms optionally including unsaturated bond(s), an aromatic or heteroaromatic ring structure having 4 to 10 ring atoms, each ring structure optionally being substituted by one or more substituents selected from heterosubstituents, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon such as aryl, aryl-($C_1$-$C_6$)-alkyl, heteroaryl-($C_1$-$C_6$)-alkyl, each hydrocarbon optionally being substituted by one or more heterosubstituents.

Preferably, $R^{1a}$, $R^{1b}$, $R^{1c}$ and $R^{1d}$ may be selected each from hydrogen, heterosubstituents, $C_1$ to $C_{20}$ straight chain, branched chain or cyclic aliphatic hydrocarbons.

$R^2$ and $R^3$ may be the same or different and may be selected each from hydrogen, $C_1$ to $C_{20}$ straight chain, branched chain or cyclic aliphatic hydrocarbons, optionally including hetero atoms and/or optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon or partially arene-hydrogenated forms such as aryl, aryl-($C_1$-$C_6$)-alkyl, heteroaryl-($C_1$-$C_6$)-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, or $C_6$ to $C_{20}$ aromatic hydrocarbon or partially arene-hydrogenated forms such as aryl, aryl-($C_1$-$C_6$)-alkyl, heteroaryl-($C_1$-$C_6$)-alkyl or heterosubstituents, and may also form a ring system between two or more $R^1$ substituents, or $R^2$ and $R^3$ may form an aliphatic or heteroaliphatic ring structure having 4 to 8 carbon atoms, said ring structure optionally being substituted by one or more substituents selected from heterosubstituents, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon such as aryl, aryl-($C_1$-$C_6$)-alkyl, heteroaryl-($C_1$-$C_6$)-alkyl, each hydrocarbon optionally being substituted by one or more heterosubstituents.

Preferably, $R^2$ and $R^3$ form an aliphatic or heteroaliphatic hydrocarbon ring structure having 4 to 8 carbon atoms, said ring structure optionally being substituted by one or more substituents selected from heterosubstituents, $C_1$ to $C_{20}$ straight chain, branched chain or cyclic aliphatic hydrocarbons $R^4$ may be selected from hydrogen, $C_1$ to $C_{20}$ straight chain, branched chain or cyclic aliphatic hydrocarbons, optionally including hetero atoms and/or optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon or partially arene-hydrogenated forms such as aryl, aryl-($C_1$-$C_6$)-alkyl, heteroaryl-($C_1$-$C_6$)-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl or heterosubstituents.

$R^N$ is a nucleophilic group selected —$OR^5$, —$NR^5R^6$ or —$CR^5R^6R^7$, wherein $R^5$, $R^6$ and $R^7$ may be the same or different and may be selected each from hydrogen, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-($C_1$-$C_6$)-alkyl, heteroaryl-($C_1$-$C_6$)-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, or $C_6$ to $C_{20}$ aromatic hydrocarbon or partially arene-hydrogenated forms such as aryl, aryl-($C_1$-$C_6$)-alkyl, heteroaryl-($C_1$-$C_6$)-alkyl or heterosubstituents, wherein at least one of $R^5$, $R^6$ and $R^7$ bears a heteroatom if $R^N$ is —$CR^5R^6R^7$, or at least two of $R^5$, $R^6$ and $R^7$ may form an aliphatic or saturated heteroaliphatic ring structure having 3 to 10 ring atoms and including unsaturated bond(s), an aromatic or heteroaromatic ring structure having 4 to 10 ring atoms, each rings structure optionally being substituted by one or more substituents selected from heterosubstituents, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon such as aryl, aryl-($C_1$-$C_6$)-alkyl, heteroaryl-($C_1$-$C_6$)-alkyl, each hydrocarbon optionally being substituted by one or more heterosubstituents, The solvent used in the inventive process may be selected from aliphatic, cycloaliphatic or aromatic solvents, alcohols, in particular lower aliphatic alcohols esters, ethers or mixtures thereof such as, for example, hexan, benzene, toluene, MeOH, DMSO, AcOH, $CH_3CN$, ethyl acetate or diethyl ether.

As catalyst, any Lewis or Brønsted acid may be used. Examples are $Fe(OTf)_3$, $Fe(NO_3)_3 \cdot 9H_2O$, $FeCl_3$, $Bi(OTf)_3$, $Yb(OTf)_3$, $Sc(OTf)_3$, $Zn(OTf)_3$, $MgCl_2$, $RuCl_3$, para-toluenesulfonic acid, $CF_3CO_2H$ or tartaric acid.

As photosensitizer, FePC or Rose Bengal may be used. Further examples of a photosensitizer are Trisbipyridyldichlororuthenium-hexahydrate, 9,10-Bis(Cyanoanthracene), Meso-Tetraphenylporphyrin, Phthalocyanine, Zinc Phthalocyanine, Copper Phthalocyanine, Iron Phthalocyanine, Methylene Blue.

A heterosubstituent as defined according to the invention can be selected from, $=O$, OH, F, Cl, Br, I, CN, $NO_2$, $SO_3H$, a monohalogenomethyl group, a dihalogenomethyl group, a trihalogenomethyl group, CF(CF3)$_2$, $SF_5$, amine bound through N atom, —O-alkyl (alkoxy), —O-aryl, —O—$SiR^S_3$, S—$R^S$, S(O)—$R^S$, S(O)$_2$—$R^S$, COOH, $CO_2$—$R^S$, amide, bound through C or N atom, formyl group, C(O)—$R^S$, COOM, where M may be a metal such as Na or K. $R^S_3$ may be, independently from each other, the same or different and may be each an aliphatic, heteroaliphatic, aromatic or heteroaromatic group, each optionally being further substituted by one or more heterosubstituents, aliphatic, heteroaliphatic, aromatic or heteroaromatic groups. Preferably, the heterosubstitunet is selected from $=O$, OH, F, Cl, Br, I, CN, $NO_2$, $SO_3H$, a monohalogenomethyl group, a dihalogenomethyl group, a trihalogenomethyl group, CF(CF3)$_2$, $SF_5$, amine bound through N atom, —O-alkyl (alkoxy), —O-aryl.

Aliphatic hydrocarbons including alkyl, alkenyl and alkinyl may comprise straight-chain, branched and cyclic hydrocarbons.

Heteroaliphatic is a hydrocarbon having 1 to 20 carbon atoms including alkyl, alkenyl and alkinyl which may comprise straight-chain, branched and cyclic hydrocarbons with one or more carbon atoms replaced or substituted with a heteroatom, preferably selected from N and O.

In more detail, $C_1$-$C_{20}$-Alkyl can be straight chain or branched and has 1, 2, 3, 4, 5, 6, 7, 8, 9, 10, 11, 12, 13, 14, 15, 16, 17, 18, 19 or 20 carbon atoms. Alkyl might be $C_1$-$C_6$-alkyl, in particular methyl, ethyl, propyl, isopropyl, butyl, isobutyl, sec-butyl or tert-butyl, likewise pentyl, 1-, 2- or 3-methylpropyl, 1,1-, 1,2- or 2,2-dimethylpropyl, 1-ethylpropyl, hexyl, 1-, 2, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Substituted alkyl groups are trifluoromethyl, pentafluoroethyl and 1,1,1-trifluoroethyl.

Cycloalkyl might be cyclopropyl, cyclobutyl, cyclopentyl, cyclohexyl or cycloheptyl. Alkenyl might be $C_2$-$C_{20}$ alkenyl. Alkinyl might be $C_2$-$C_{20}$ alkinyl.

Halogen is F, Cl, Br or I.

Alkoxy is preferably $C_2$-$C_{10}$ alkoxy such as methoxy, ethoxy, propoxy, tert-butoxy etc.

$C_3$-$C_8$-Heterocycloalkyl having one or more heteroatoms selected from among N, O and S is preferably 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Optionally substituted means unsubstituted or monosubstituted, disubstituted, trisubstituted, tetrasubstituted, pentasubstituted, or even further substituted for each hydrogen on the hydrocarbon.

Aryl might be phenyl, naphthyl or biphenyl.

Arylalkyl might be benzyl.

Heteroaryl having one or more heteroatoms selected from among N, O and S is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-Indolyl, 4- or 5-isoindolyl, 1-, 2-, 4- or 5-benz-imidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, also preferably 1,3-benzodioxol-5-yl, 1,4-benzodioxan-6-yl, 2,1,3-benzothiadiazol-4- or -5-yl or 2,1,3-benzoxadiazol-5-yl.

In the above formulae, the substituents $R^1$, $R^2$, $R^3$ $R^4$, $R^5$, $R^6$ and $R^N$ may have the meaning as follows:

$R^1$: Hydrogen, alkyl, such as methyl, ethyl, or substituted alkyl, F, Cl, Br, CN, $NO_2$, $-CF_3$;

$R^2$, $R^3$: Alkyl, or $R^2$ and $R^3$ form a ring structure as defined above, all the afore optionally substituted with heterosubstituents;

$R^4$: Hydrogen $R^N$: $-NR^5R^6$ $R^5$: Hydrogen or alkyl, optionally being substituted by heterosubstituents $R^6$: Aryl, optionally being substituted by heterosubstituents.

DETAILED DESCRIPTION OF THE INVENTION

In a first embodiment of the inventive method, a direct coupling from (I) to (IV) ("direct coupling") takes place whereas, in the second embodiment, a two-step sequence ("two-step coupling") is involved. In either embodiment, use is made of a reactive hydroperoxide species (III) formed as intermediate by the reaction of the indole ring system with oxygen. In the first embodiment, this intermediate is not isolated ("direct coupling"), in the second embodiment, the intermediate is isolated and further transformed to the final product in a second reaction step ("two-step coupling").

In the first embodiment, compound (I) is usually reacted with compound (II) in the presence of a catalyst, for example iron phthalocyanine (FePc), and oxygen in a solvent such as methanol to yield product (IV), usually in a yield of more than 50%.

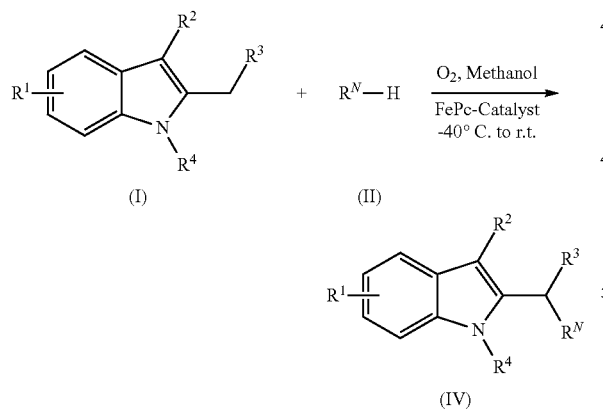

The reaction proceeds well with irradiation by a lamp, sunlight or even in the dark. As outlined below for the second embodiment, the reaction requires the action of a photocatalyst and an acid catalyst. Only one catalyst compound is required if it combines the properties of both photocatalyst and acid. An example for this combination of properties is FePc.

The inventors assume that the reaction proceeds in the same manner as the coupling method in second embodiment, i.e. via intermediate a hydroperoxide (III) as detailed below.

In said second embodiment of the inventive method, the inventive coupling method proceeds in two steps with an intermediate (III), usually a hydroperoxide, but also a mixture of peroxide and hydroxide derivatives.

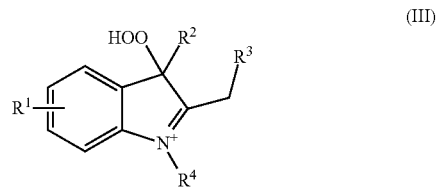

In the first step, the substrate (I) is transformed to intermediate (III) by the action of singlet oxygen, for example, by reacting (I) with oxygen in the presence of a sensitizer like rose bengal or tetraphenylporphyrine under irradiation by a lamp or sunlight in a solvent such as toluene at room temperature in the range of 15° to 25° C. The intermediate can be directly employed in the second step without purification. A change of solvent to methanol or acetic acid is usually necessary if the oxidation step is performed in another solvent. In the second step, the intermediate (III) is transformed to the product (IV) by reacting with a nucleophile in the presence of a Lewis or Brønsted acid. The inventors have found that two separate catalysts, one photocatalyst and one acid catalyst, give the best results in the second embodiment ("two-step coupling").

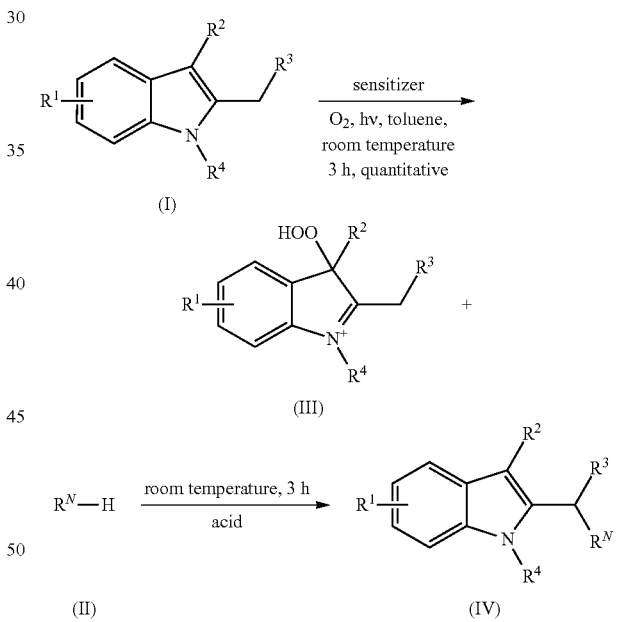

In said reaction scheme, intermediate (III) may comprise a mixture of peroxide (IIIa,b) and hydroxide derivatives (IIIc, d).

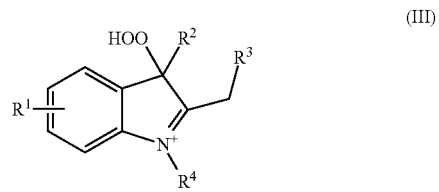

-continued

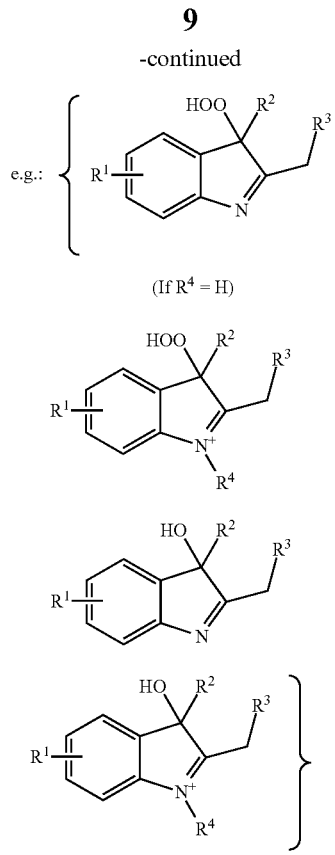

| Entry | Product | $R^1$ | $R^9$ | R8 | Yield (%) |
|---|---|---|---|---|---|
| 1 | 5 | H | $NO_2$ | H | 50 |

For the second embodiment, the product with the product number as indicated in the following table and having the general formula (V) was obtained by "coupling in two steps":

| Entry | Product | $R^1$ | $R^9$ | $R^8$ | Method | Yield (%) | d.r. |
|---|---|---|---|---|---|---|---|
| 1 | 1 | H | H | H | AcOH | 90 | — |
| 2 | 2 | H | Ph | H | Tfa/MeOH | 50 | — |
| 3 | 3 | H | CN | H | AcOH | 90 | — |
| 4 | 4 | H | COPh | H | AcOH | 74 | — |
| 5 | 5 | H | $NO_2$ | H | Tfa/MeOH | 70 | — |
| 6 | 6 | H | $OCF_3$ | H | AcOH | 60 | — |
| 7 | 7 | H | F | H | AcOH | 71 | — |
| 8 | 8 | H | Cl | H | AcOH | 70 | — |
| 9 | 9 | CN | CN | H | Tfa/MeOH | 50 | — |
| 10 | 10 | F | CN | H | Tfa/MeOH | 73 | — |
| 11 | 11 | Cl | CN | H | Tfa/MeOH | 90 | — |
| 12 | 12 | Br | CN | H | Tfa/MeOH | 80 | — |
| 13 | 13 | Br | F | H | AcOH | 60 | — |
| 14 | 14 | H | $NO_2$ | Me | Tfa/MeOH | 67 | 91:9 |
| 15 | 15 | H | $NO_2$ | Ph | Tfa/MeOH | 65 | 83:17 |

Further experiments for the inventive method making use of the two-step process lead under similar conditions to the products and respective yields as represented in the following scheme:

For the second embodiment of the inventive method, three variants for the second step have been found to be particularly useful, depending on the nucleophile:

1) "Tfa/MeOH": methanol as solvent, 10 mol % Tfa/$CF_3CO_2H$ as catalyst
2) "AcOH": $CH_3CO_2H$ as solvent, no additional catalyst
3) "MeOH": methanol as solvent, no additional catalyst It appeared to the inventors that an additional catalyst will not be needed in case that the compound (II). i.e. the nucleophilic compound is sufficiently acid to act as an acid catalyst.

The inventors have carried out several experimental tests for evaluating the scope of the inventive method. The results are summarized in the following schemes. In said formula (V), $R^9$ has the meaning as given for $R^1$ above and R8 the meaning of alkyl, particularly methyl, or phenyl as exemplified in the following.

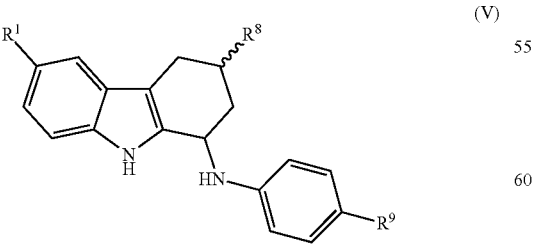

For the first embodiment, the product with the product number as indicated in the following table and having the general formula (V) was obtained by "direct coupling":

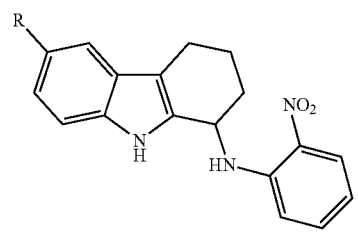

Tfa/MeOH
16, R = H, 86%
17, R = Cl, 55%

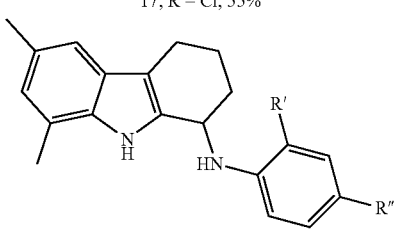

Tfa/MeOH
18, R' = $NO_2$, R" = H, 26%
19, R' = H, R" = $NO_2$, 86%

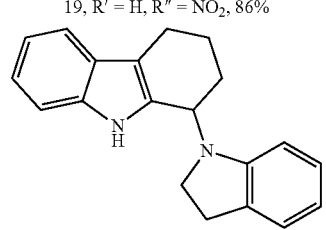

AcOH
20, 50%

-continued

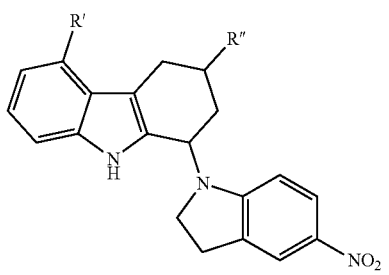

Tfa/MeOH
21, R' = R" = H, 95%
22, R' = Cl, R" = H, 70%
23, R' = H, R" = Me, 90%, 85:15 dr

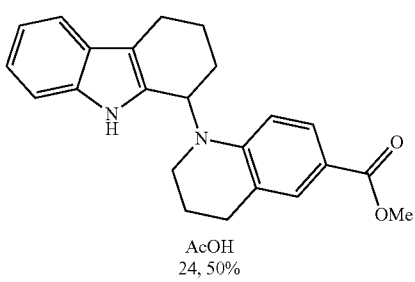

AcOH
24, 50%

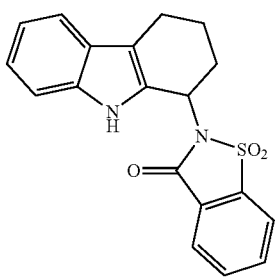

MeOH
25, 52%

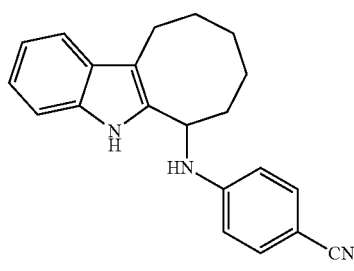

Tfa/MeOH
26, 50%

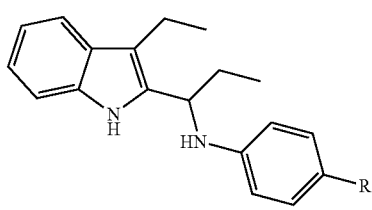

AcOH
27, R = NO$_2$, 25%
28, R = CN, 45%

-continued

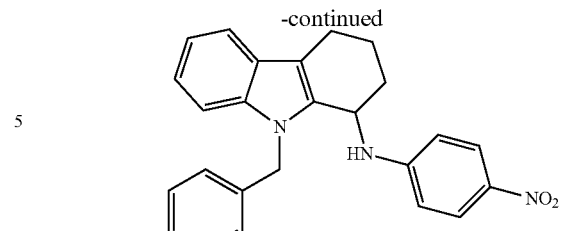

Tfa/MeOH
29, 20%

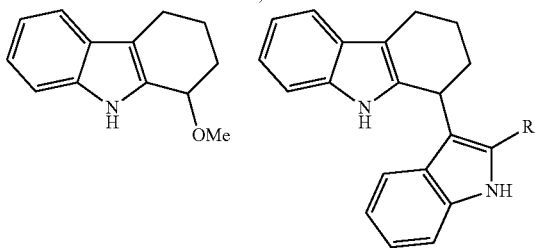

Tfa/MeOH
30, 80%

Tfa/MeOH
31, R = Me, 95%
32, R = CHO, 40%

The inventors have thus established a novel straightforward method for producing substituted indole derivatives in a fast an efficient way with high yields.

The invention claimed is:

1. A process for preparing an indole derivative of the formula (IV) without the use of dimethylsulfide, said process comprising reacting an indole-derivative with a C—H-group in the 2-position of the formula (I) with a nucleophilic compound $R^N$—H of the formula (II) in a solvent and with oxygen in the presence of at least one catalyst:

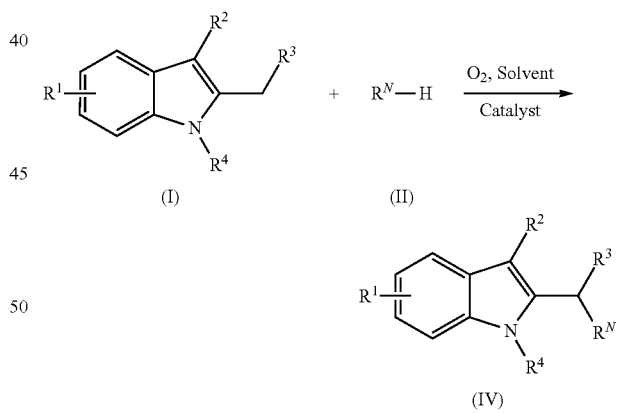

wherein $R^1$ represents four substituents $R^{1a}$, $R^{1b}$, $R^{1c}$ and $R^{1d}$ on the aromatic ring which substituents may be the same of different and may be selected each from hydrogen, heterosubstituents, $C_1$ to $C_{20}$ straight chain, branched chain or cyclic aliphatic hydrocarbons, optionally including hetero atoms and/or optionally having one or more unsaturated, $C_3$-$C_8$-heterocycloalkyl or $C_6$ to $C_{20}$ aromatic hydrocarbon or partially arene-hydrogenated forms, each heterosubstituent or hydrocarbon optionally being substituted by one or more groups selected from $C_1$ to $C_{20}$ straight chain, branched chain or cyclic aliphatic hydrocarbons, optionally including hetero atoms and/or optionally having one or more unsaturated bonds, or $C_6$ to $C_{20}$ aromatic hydrocarbon or partially arene-hydrogenated forms or heterosubstituents, or at least two of said $R^{1a}$, $R^{1b}$, $R^{1c}$ and $R^{1d}$ substituents may also form an aliphatic or heteroaliphatic ring structure having 4 to 10 ring atoms optionally including unsaturated bond(s), an aromatic or heteroaromatic ring structure having 4 to 10 ring atoms, each ring structure optionally being substituted by one or more substituents selected from heterosubstituents, $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon, each hydrocarbon optionally being substituted by one or more heterosubstituents;

$R^2$ and $R^3$ may be the same or different and may be selected each from hydrogen, $C_1$ to $C_{20}$ straight chain, branched chain or cyclic aliphatic hydrocarbons, optionally including hetero atoms and/or optionally having one or more unsaturated bonds, $C_3$-$C_8$-heterocycloalkyl or $C_6$ to $C_{20}$ aromatic hydrocarbon or partially arene-hydrogenated forms, each hydrocarbon optionally being substituted by one or more groups selected from $C_1$ to $C_{20}$ straight chain, branched chain or cyclic aliphatic hydrocarbons, optionally having one or more unsaturated bonds, or $C_6$ to $C_{20}$ aromatic hydrocarbon or partially arene-hydrogenated forms or heterosubstituents, and may also form a ring system between two or more $R^1$ substituents, or $R^2$ and $R^3$ may form an aliphatic or heteroaliphatic ring structure having 4 to 8 carbon atoms, said ring structure optionally being substituted by one or more substituents selected from heterosubstituents, $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon, each hydrocarbon optionally being substituted by one or more heterosubstituents;

$R^4$ may be selected from hydrogen, $C_1$ to $C_{20}$ straight chain, branched chain or cyclic aliphatic hydrocarbons, optionally including hetero atoms and/or optionally having one or more unsaturated bonds, $C_3$-$C_8$-heterocycloalkyl or $C_6$ to $C_{20}$ aromatic hydrocarbon or partially arene-hydrogenated forms, each hydrocarbon optionally being substituted by one or more groups selected from $C_1$ to $C_{20}$ straight chain, branched chain or cyclic aliphatic hydrocarbons, optionally having one or more unsaturated bonds, or $C_6$ to $C_{20}$ aromatic hydrocarbon and partially arene-hydrogenated forms or heterosubstituents;

$R^N$ is a nucleophilic group selected from —$OR^5$, —$NR^5R^6$ or —$CR^5R^6R^7$, wherein $R^5$, $R^6$ and $R^7$ may be the same or different and may be selected each from hydrogen, $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon and partially arene-hydrogenated forms, each hydrocarbon optionally being substituted by one or more groups selected from $C_1$ to $C_{20}$ straight chain, branched chain or cyclic aliphatic hydrocarbons, optionally having one or more unsaturated bonds, or $C_6$ to $C_{20}$ aromatic hydrocarbon or partially arene-hydrogenated forms or heterosubstituents, wherein at least one of $R^5$, $R^6$ and $R^7$ bears a heteroatom if $R^N$ is —$CR^5R^6R^7$, or at least two of $R^5$, $R^6$ and $R^7$ may form an aliphatic or saturated heteroaliphatic ring structure having 3 to 10 ring atoms and including unsaturated bond(s), an aromatic or heteroaromatic ring structure having 4 to 10 ring atoms, each rings structure optionally being substituted by one or more substituents selected from heterosubstituents, $C_1$ to $C_{20}$ straight chain, branched chain or cyclic aliphatic hydrocarbons, optionally having one or more unsaturated bonds, $C_3$-$C_8$-heterocycloalkyl or $C_6$ to $C_{20}$ aromatic hydrocarbon, each hydrocarbon optionally being substituted by one or more heterosubstituents, wherein the process is conducted without the use of dimethylsulfide.

2. Process according to claim 1, wherein the catalyst is a photosensitizer and the reaction is carried under irradiation with light.

3. Process according to claim 2, wherein compound (I) is converted, under the action of oxygen and irradiation with light in the presence of a photosensitizer, into the hydroperoxide compound of the formula (III) which is further reacted with the nucleophilic compound $R^N$—H of the formula (II) to yield compound (IV):

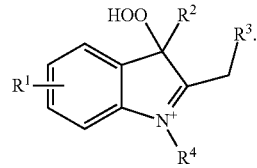

(III)

4. Process according to claim 2, wherein the photosensitzer is selected from Rose Bengal, Trisbipyridyldichlororuthenium-hexahydrate, 9,10-Bis(Cyanoanthracene), Meso-Tetraphenylporphyrin, Phthalocyanine, Zinc Phthalocyanine, Copper Phthalocyanine, Iron Phthalocyanine, or Methylene Blue.

5. Process according to claim 1, wherein the reaction is carried out in the presence of a Lewis acid or Brønsted acid as catalyst.

6. Process according to claim 1, wherein said $C_1$ to $C_{20}$ straight chain, branched chain or cyclic aliphatic hydrocarbons are independently selected from the group consisting of $C_1$-$C_{20}$-alkyl, $C_2$-$C_{20}$-alkenyl and $C_2$-$C_{20}$-alkinyl.

7. Process according to claim 1, wherein said $C_6$ to $C_{20}$ aromatic hydrocarbon and partially arene-hydrogenated forms are independently selected from the group consisting of aryl, aryl-($C_1$-$C_6$)-alkyl and heteroaryl-($C_1$-$C_6$)-alkyl.

8. Process according to claim 1, wherein said heterosubstituents are independently selected from the group consisting of =O, OH, F, Cl, Br, I, CN, $NO_2$, $SO_3H$, a monohalogenomethyl group, a dihalogenomethyl group, a trihalogenomethyl group, $CF(CF3)_2$, $SF_5$, amine bound through N atom, —O-alkyl (alkoxy) and —O-aryl.

* * * * *